(12) United States Patent
Schütz et al.

(10) Patent No.: US 6,475,737 B1
(45) Date of Patent: Nov. 5, 2002

(54) METHOD OF AUTOMATICALLY SELECTING OLIGONUCLEOTIDE HYBRIDIZATION PROBES

(76) Inventors: Ekkehard Schütz, Beekweg 23, D - 37079 Göttingen (DE); Nicolas von Ahsen, Stumpfe Eiche 4, D - 37077 Göttingen (DE)

( * ) Notice: Subject to any disclaimer, the term of this patent is extended or adjusted under 35 U.S.C. 154(b) by 0 days.

(21) Appl. No.: 09/717,569

(22) Filed: Nov. 21, 2000

(30) Foreign Application Priority Data

Nov. 24, 1999 (EP) .............................................. 99123393

(51) Int. Cl.$^7$ ........................... C12Q 1/68; C12P 19/34; C07H 21/02; C07H 21/04; G01N 33/48

(52) U.S. Cl. .......................... 435/6; 435/91.1; 435/91.2; 536/22.1; 536/23.1; 536/24.3; 536/24.31; 536/24.32; 536/24.33; 702/19; 702/20

(58) Field of Search ............................. 435/6, 7.1, 91.1, 435/91.2, 287.2; 536/22.1, 23.1, 24.3, 24.31, 24.32, 24.33; 702/19, 20

(56) References Cited

U.S. PATENT DOCUMENTS

| | | | |
|---|---|---|---|
| 5,556,749 A | 9/1996 | Mitsuhashi et al. ............. | 435/6 |
| 5,856,103 A | 1/1999 | Gray et al. ..................... | 435/6 |

FOREIGN PATENT DOCUMENTS

| | | |
|---|---|---|
| WO | PCT/US97/19673 | 10/1997 |

OTHER PUBLICATIONS

SantaLucia et al. "Improved Nearest–Neighbor Parameters for Predicting DNA Duplex Stability," Biochemistry, US, American Chemical Society, Easton, PA, vol. 35, Jan. 1, 1996, pp. 3555–3562; abstract, p. 3561.

Giesen et al. "A formula for thermal stability (Tm) prediction of PNA/DNA duplexes" Nucleic Acids Research, GB, Oxford University Press, Surrey, vol. 26, No. 21, Jan. 1, 1998, pp. 5004–5006.

Doktycz et al. "Optical Melting for 128 Octamer DNA Duplexes, Effects of Base Pair Location and Nearest Neighbors on Thermal Stability," Journal of Biological Chemistry, US, American Society of Biological Chemists, Baltimore, MD, vol. 270, No. 15, Apr. 14, 1995, pp. 8439–8445.

B. E.Caplin, A. Rasmussen, P.S. Bernard, and C.T. Wittwer (1999) "LightCycler Hybridization Probes," *Biochemica* 1: 5–8.

D.M. Gray (1997) "Derivation of Nearest–Neighbor Properties from Data on Nucleic Acid Oligomers. I. Simple Sets of Independent Sequences and the Influence of Absent Nearest Neighbors," *Biopolymers* 42: 783–793.

H.T. Allawi and J. SantaLucia, Jr. (1997) Thermodynamics and NMR of Internal G•T Mismatches in DNA, Biochemistry 36: 10581–10594.

J. Santa Lucia, Jr., H.T. Allawi, and P.A. Seneviratne (1996) "Improved Nearest–Neighbor Parameters for Predicting DNA Duplex Stability," Biochemistry 35: 3555–3562.

J. SantaLucia, Jr. (1998) "A Unified View of Polymer, Dumbbell, and Oligonucleotide DNA Nearest_neighbor Thermodynamics," Proc Natl Acad Sci USA 95: 1460–1465.

N. Sugimoto, S. Nakano, M. Yoneyama and K. Honda (1996) "Improved Thermodynamics Parameters and Helix Initiation Factor to Predict Stability of DNA Duplexes," Nucleic Acids Res 24:4501–4505.

H.T. Allawi and J. SantaLucia, Jr. (1998) "Nearest–Neighbor Thermodynamics of Internal A•C Mismatches in DNA: Sequence Dependence and pH Effects," Biochemistry 37: 9435–9444.

H.T. Allawi and J. SantaLucia, Jr. (1998) "Thermodynamics of Internal C•T Mismatches in DNA," Nucleic Acids Res 26: 2694–2701.

H.T. Allawi and J. SantaLucia, Jr. (1998) "Nearest Neighbor Thermodynamic Parameters for Internal G•A Mismatches in DNA," Biochemistry 37: 2170–2179.

N. Peyret, P.A. Seneviratne, H.T. Allawi, and J. SantaLucia, Jr. (1999) "Nearest–Neighbor Thermodynamics and NMR or DNA Sequences with internal A•A, C•C, G•G, and T•T Mismatches," Biochemistry 38: 3468–3477.

R. Owczarzy, P.M. Vallone, F.J. Gallo, T.M. Paner, M.J. Lane, and A.S. Benight (1997) "Predicting Sequence–Dependent Melting Stability of Short Duplex DNA Oligomers," Biopolymers 44: 217–239.

S. Nakano, M. Fujimoto, H. Hara, and N. Sugimoto (1999) "Nucleic Acid Duplex Stability: Influence of Base Composition on Cation Effects," Nucleic Acids Res 27: 2957–2965.

N. Chester and D.R. Marshak (1993) "Dimethyl Sulfoxide–Mediated Primer Tm Reduction: A Method for Analyzing the Role of Renaturation Temperature in the Polymerase Chain Reaction," Anal Biochem 209: 284–290.

(List continued on next page.)

*Primary Examiner*—Jeffrey Siew
(74) *Attorney, Agent, or Firm*—George M. Thomas; Thomas, Kayden, Horstemeyer & Risley (57) ABSTRACT

A method for automatically selecting oligonucleotide hybridization probes for detecting a mutation causing a mismatch in a DNA duplex is based on a thermodynamic nearest-neighbour model for calculating a melting point, which is a temperature at which a predetermined percentage of a multitude of identical hybridized pairs of a certain hybridization probe and a DNA strand is in an annealed state. Using this model a first melting point of the respective probe hybridized with its complementary mutant DNA strand or opposite sense mutant DNA strand, a second melting point of the respective probe hybridized with its complementary wild-type DNA strand or opposite sense wild-type DNA strand, respectively, and a temperature difference between the first and second melting points are calculated for all possible hybridization probes. Then, the possible hybridization probes are ranked with regard to the calculated temperature difference.

10 Claims, 6 Drawing Sheets

OTHER PUBLICATIONS

H. Musielski, W. Mann, R. Laue, and S. Michel (1981) "Influence of Dimethylsulfoxide on Transcription by Bacteriophage T3–Induced RNA Polymerase," Z Allg Mikrobiol abstract.

P.S. Bernard, M.J. Lay, C.T. Wittwer (1998) "Integrated Amplification and Detection of the C677T Point Mutation in the Methylenetetrahydrofolate Reductase Gene by Fluorescence Resonance Energy Transfer and Probe Melting Curves," Anal Biochem 255:101–107.

P.S. Bernard, R.S. Ajioka, J.P. Kushner, and C.T. Wittwer (1998) "Homogeneous Multiplex Genotyping of Hemochromatosis Mutations with Fluorescent Hybridization Probes," Am J. Pathol 153: 1055–1061.

P.S. Bernard, G.H. Pritham, and C.T. Wittwer (1999) "Color Multiplexing Hybridization Probes Using the Apolipoprotein E Locus as Model System for Genotyping," Biochem 173:221–228.

M.J. Lay and C.T. Wittwer (1997) "Real–Time Fluorescence Genotyping of Factor V Leiden During Rapid–Cycle PCR," Clin Chem 43: 2262–2267.

E. Lyon, A. Misson, T. Phan, and C.T. Wittwer (1998) "Detection and Identification of Base Alterations Within the Region of Factor V Leiden by Fluorescent Melting Curves," Mol Diagn 3: 203–209.

C. Aslanidis and G. Schmitz (1999) "High–Speed Apolipoprotein E Genotyping and Apolipoprotein B3500 Mutation Detection Using Real–Time Fluorescence PCR and Melting Curves," Clin Chem 45: 1094–1097.

C. Aslanidis, M. Nauck, and G. Schmitz (1999) "High–Speed Prothrombin G—> A 20210 and Methylenetetrahydrofolate Reductase C—> 677 Mutation Detection Using Real–Time Fluoresence PCR and Melting Curves," Biotechniques 27: 234–6, 238.

D. Gaffney, J.M. Reid, I.M. Cameron, K. Vass, M.J. Caslake, J. Sheperd, and C.J. Packard (1995) "independent Mutations at Codon 3500 of the Apolipoprotein B Gene are Associated with Hyperlipidemia," Arterioscler Thromb Vasc Biol 15: 1025–1029.

N. von Ahsen, E. Schütz, V.W. Armstrong, and M. Oellerich (1999) "Rapid Detection of Prothrombotic Mutations of Prothrombin (G20210A), Facotr V (G1691A) and Methylenetetrahydrofolate Reductase (C677T) by Real Time Fluoresence PCR with the LightCycler," Clin Chem 45: 694–696.

M. Nauck, H. Wieland, and W. März (1999) "Rapid, Homogeneous Genotyping of the 4G/5G Polymorphism in the Promoter Region of the PAI1 Gene by Fluorescence Resonance Energy Transfer and Probe Melting Curves," Clin Chem 45: 1141–1147.

M.S. Nauck, H. Gierens, M.A. Nauck, W. Marz, and H. Wieland (1999) "Rapid Genotyping of Human Plateflet Antigen 1 (HPA–1) with Fluorophore–labelled Hybridization Probes on the LightCycler," Br J Haematol 105: 3803–810.

A. Tybjaerg–Hansen, R. Steffensen, H. Meinertz, P. Schnohr, and B.G. Nordestgaard (1998) "Association of Mutations in the Apolipoprotein B Gene with Hypercholesterolemia and the Risk of Ischemic Heart Disease," N Engl J Med 338: 1577–1584.

H.A. Liebman, D. Sutherland, R. Bacon, and W. McGehee (1996) "Evaluation of a Tissue Factor Dependent Factor V Assay to Detect Factor V Leiden: Demonstration of High Sensitivity and Specificity for a Generally Applicable Assay for Activated Protein C Resistance," Br J Haematol 95: 550–553.

M. Cargill, D. Altshuler, J. Ireland, P. Sklar, K. Ardlie, N. Patil, C.R. Lane, E.P. Lim, N. Kalayanaraman, J. Nemesh, L. Ziaugra, L. Friedland, A. Rolfe, J. Warrington, R. Lipshultz, G.Q. Daley, and E.S. Lander (1999) "Characterization of Single–Nucleotide Polymorphisms I Coding Regions of Human Genes," Nat Genet 22: 231–238.

S.M. Brown (1999) "Snapping up SNPs," Biotechniques 26: 1090–1093.

D.N. Cooper, M. Krawczak and S.E. Antonarakis (1995) "The Nature and Mechanism of Human Gene Mutation. In: The Metabolic and Molecular Bases of Inherited Disease," edited by C.R. Scriver, et al., pp. 259–291. McGraw–Hill, New York.

R.M. Clegg (1995) "Fluorescence Resonance Energy Transfer," Curr Opin Biotechnol 6: 103–100.

H. Passing and W. Bablock (1984) "Comparison of Several Regression Procedures for Method Comparison Studies and Determination of Sample Sizes. Application of Linear Regression Procedures for Method Comparison Studies in Clinical Chemistry, Part II," J Clin Chem Clin Biochem 22: 431–445.

European Search Report, May 23, 2000, 2 pages.

METHOD OF AUTOMATICALLY SELECTING OLIGONUCLEOTIDE HYBRIDIZATION PROBES

FIELD OF THE INVENTION

The invention relates to a method of automatically selecting oligonucleotide hybridization probes for detecting a mutation causing a mismatch in a DNA duplex.

BACKGROUND OF THE INVENTION

The hybridization of oligonucleotide hybridization probes is a technique with widespread application in molecular biology. It has been used for the detection of immobilized nucleic acids in northern or southern blotting and for allele specific oligonueleotide hybridization. Provided stringency conditions are met, only a perfect complementary hybridization probe will basepair with the DNA strand, observed. The method can therefore be used for mutation detection when the presence of a mismatch caused by a base exchange disrupts the Watson-Crick pairing and destabilizes the partial duplex formed by the hybridization probe and the DNA strand observed.

A known possible tool for monitoring the hybridization of a labeled hybridization probe to a DNA strand to be observed in an homogenous assay is the LightCycler (Trademark, manufactured by Roche Molecular Biochemicals). Three different wavelengths are available for the optical detection of oligonucleotide hybridization when an appropriate fluorescence resonance energy transfer (FRET) pair is formed by adjacent hybridization of two dye labeled hybridization probes with the DNA strand to be observed. One of the two hybridization probes is called the anchor probe while the other probe which is directly sensitive to the mutation to be detected is called the detection probe. The monitored fluorescence signal is proportional to the amount of the hybridized hybridization probe pairs. The temperature at which a certain percentage (normally 50%) of the hybridization probe pairs is hybridized or in a so-called annealed state is called the melting point Tm of the hybridization probe pair. This melting point can also be regarded as the melting point of only the detection probe as the melting point of the anchor probe is typically set to be considerably higher than that of the detection probe.

For mutation detection the Tm shift caused by the mutation should be as high as possible to ensure good discrimination of heterozygotes.

General guidelines for the construction of hybridization probes for use in both, quantification and mutation detection, have been given [1], but these depend on an accurate estimation of DNA melting temperatures.

The melting temperature of short (<20 bp) oligonucleotides is often estimated with the Wallace/Ikatura rule Tm=2° C. (A-T bp)+4° C. (G-C bp). Although this approximation assumes a salt concentration of 0.9M NaCl, typical for dot blots and other hybridizations, it also works well for PCR applications which are not very sensitive to different Tms. However, for hybridization probes a more accurate estimation of Tm is required.

From U.S. Pat. No. 5,556,749 it is known to automatically select oligonucleotide hybridization probes taking their respective melting points into consideration. However, this known method proves not to be accurate.

Therefore, it is an object of this invention to provide a method of automatically selecting oligonucleotide hybridization probes for detecting a mutation causing a mismatch in a DNA duplex by a sufficient accurate estimation of their Tm.

This object is achieved by a method according to claim 1.

Advantageous embodiments of this method are outlined in the subclaims 2 to 10.

The nearest-neighbor (n-n) model is based on thermodynamic calculations and gives the most precise prediction of oligonucleotide stability. This model assumes that the thermodynamic parameters for a given pair depend only on the identity of its adjacent pair and that these nearest neighbor parameters are pairwise additive. The stability of a given oligonucleotide sequence is a function of two basic sources, the sum of the interstrand H bonding between Watson-Crick paired bases and the intrastrand base stacking. The application of this model for calculation of DNA duplex stability will be detailed in the methods section of this chapter. The derivation of the used formula E can be found in the literature [2] and will not be given here. Several data sets are now available that describe the ten n-n pairs that occur in double stranded oligonucleotide DNA [3–6]. The contribution of a mismatch to the duplex stability depends on the location and orientation and on the neighboring bases as well [3]. The destabilizing effect of the 48 possible single mismatches can also be taken into account if the n-n data of the respective mismatches are used for the calculation of the melting temperature [3; 7–10]. Oligonucleotides with repetitive sequences or strings of A-T base pairs may deviate from the n-n model as well as molecules which do not melt in a two state (all or nothing) manner (11). Hybridization conditions (ionic strength and probe concentration) also influence the Tm and must be considered. It could be proved that the n-n model is able to predict the melting points observed with hybridization probe assays with a standard error of less than 1° C. The n-n model is most beneficial for the thermodynamic predictions of oligonucleotide DNA. In longer DNA strands, interactions that are independent of the neighboring bases become increasingly important. This reduces the utility of the n-n model for the prediction of longer (>150 bp) DNA duplexes.

In the following the invention will be described in more detail with regard to preferred embodiments of the new method. Further, a brief description on how thermodynamic data for use in the new method can be calculated will be given. Next, the application of the n-n model to hybridization probe assays on the LightCycler will be validated. At last a general comment will be given on sensitivity and specificity of hybridization probes selected by the new method.

Figure 1:
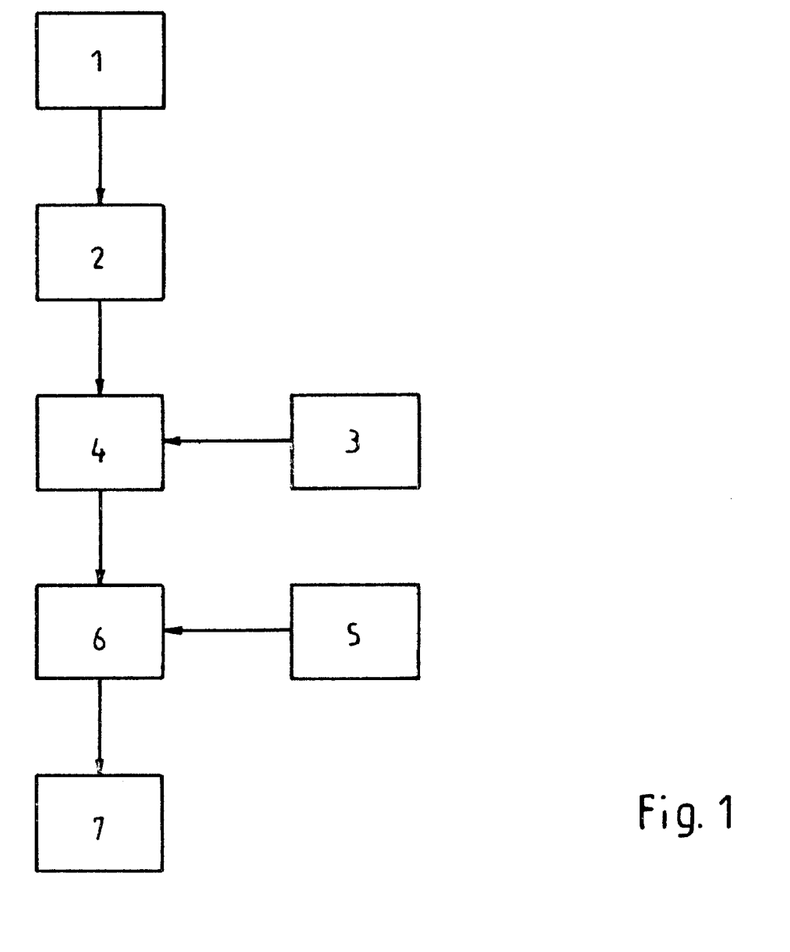
FIG. 1 is a flux diagram of a first embodiment of the new method.

As indicated in FIG. 1, a method of automatically selecting oligonucleotide hybridization probes for detecting a mutation causing a mismatch in a DNA duplex starts with the step 1 of defining the mutation to be detected by a DNA sequence of a mutant DNA strand and a DNA sequence of a wild-type DNA strand corresponding to the mutant DNA strand. Here, it is unimportant whether the mutant DNA strand and the wild-type DNA strand are sense or antisense strands as the sense strard always defines the antisense strand and vice versa. In the following as well as in the claims a term opposite sense strand is used to refer to the strand having the sense opposite to the strand dined in step 1. Therefore, opposite sense strand is no other formulation for antisense strand but may also refer to a sense strand.

In step 2 of the method integer variables L1 and L2 are defined for a first and a second lengths of the oligonucleotide hybridization probes from the place of mutation in a first and a second direction opposite to the first direction. Further, ranges from m1 to n1 and from m2 to n2 of possible values of the variables L1 and L2, respectively, are defined.

Alternatively, step 2 can include defining a first variable for an end point of the oligonucleotide hybridization probes being located from the place of mutation in a first direction; and defining a second variable for a length of the hybridization probes in a second direction opposite to the first direction. Then, first and second ranges are to be defined for the first and the second variables, in which the second range is dependent of the first range as the hybridization probes have in any case to cover the place of mutation.

At least in the end, both alternatives of step 2 have the same results. Therefore, they are in the following as well as in the claims regarded as identical.

In step 3 one or more kind(s) of the oligonucleotide hybridization probes are selected from probes which have an one-to-one hybridization fit to the mutant DNA strand, probes which have an one-to-one hybridization fit to the wild-type DNA strand corresponding to the mutant DNA strand, probes which have an one-to-one hybridization fit to an opposite sense mutant DNA strand which is the complementary DNA strand to the mutant DNA strand, and probes which have an one-to-one hybridization fit to an opposite sense wild-type DNA strand which is the complementary DNA strand to the wild-type DNA strand corresponding to the mulant DNA strand.

All of the above kinds can be selected, if no special requirements are given. If such requirements exist, special kinds of the oligonucleotide hybridization probes can be selectively selected or deselected.

In step 4 all possible hybridization probes are determined from the input data of steps 2 and 3, i.e. from the possible values of the variables L1 and L2, and the kind(s) of probes.

In step 5 a thermodynamic nearest-neighbor (n-n) model for calculating a melting point of a certain hybridization probe hybridized to a DNA strand is defined. That n-n model will be discussed in detail below. The melting point is a temperature at which a predetermined percentage of a multitude of identical pairs of said certain hybridization probe and said DNA strand is in an annealed state, i.e. hybridized.

In step 6, on basis of the thermodynamic nearest-neighbor model, the following values are calculated for all possible hybridization probes:

a first melting point of the respective probe hybridized with its complementary mutant DNA strand or opposite sense mutant DNA strand, respectively, a second melting point of the respective probe hybridized with its complementary wild-type DNA strand or opposite sense wild-type DNA strand, respectively, and a temperature difference between the second melting point and the first melting point.

At last, in step 7, the possible hybridization probes are ranked with regard to the temperature difference, and a ranked list of the hybridization probes is output.

Figure 2:
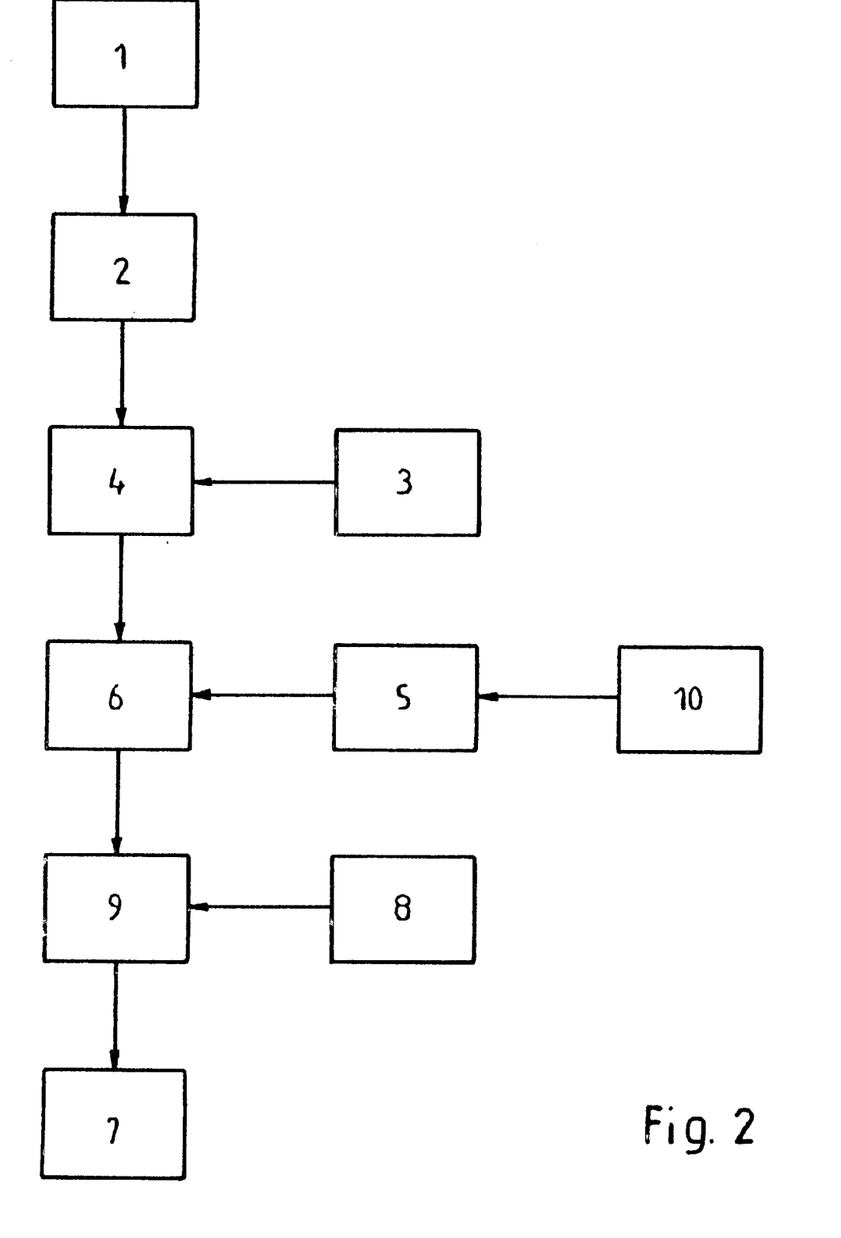
FIG. 2 is a flux diagram of a second embodiment of the net method.

According to FIG. 2, a preferred embodiment of the new method further includes step 8 in which a temperature range of a hybridization assay to be employed for detecting the mutation using the oligonucleotide hybridization probes is defined. Then in step 9 following step 6 and preceding step 7, it is checked for each of the possible hybridization probes whether both the first and the second melting points are within the temperature range of the hybridization assay. Here, in step 7 only those possible hybridization probes are ranked which have both their melting points within the temperature range of the hybridization assay.

As the maximum Tm shift caused by the mutation is limited, it is also sufficient to define a narrower temperature range in step 8, and to only check whether that melting point corresponding to the narrower temperature range is within said temperature range.

The actual temperature range is dependent of the hybridization assay to be employed. However, it will normally be defined within a range from 20 to 80° C.

According to FIG. 2, a further step 10 is added to the method according to FIG. 1 In step 10 at least one physicochemical parameter of the hybridization assay to be employed for detecting the mutation using the oligonucleotide hybridization probes is additionally defined, Correspondingly, step 5 includes defining the thermodynamic nearest-neighbor model dependently of the at least one physico-chemical parameter of the hybridization assay. The at least one physico-chemical parameter of the hybridization assay can for example be an ion concentration under which the hybridization of the hybridization probes is to be monitored. Such an ion concentration can be a total cation concentration denoted as a Na+ cation equivalent concentration.

Figure 3:
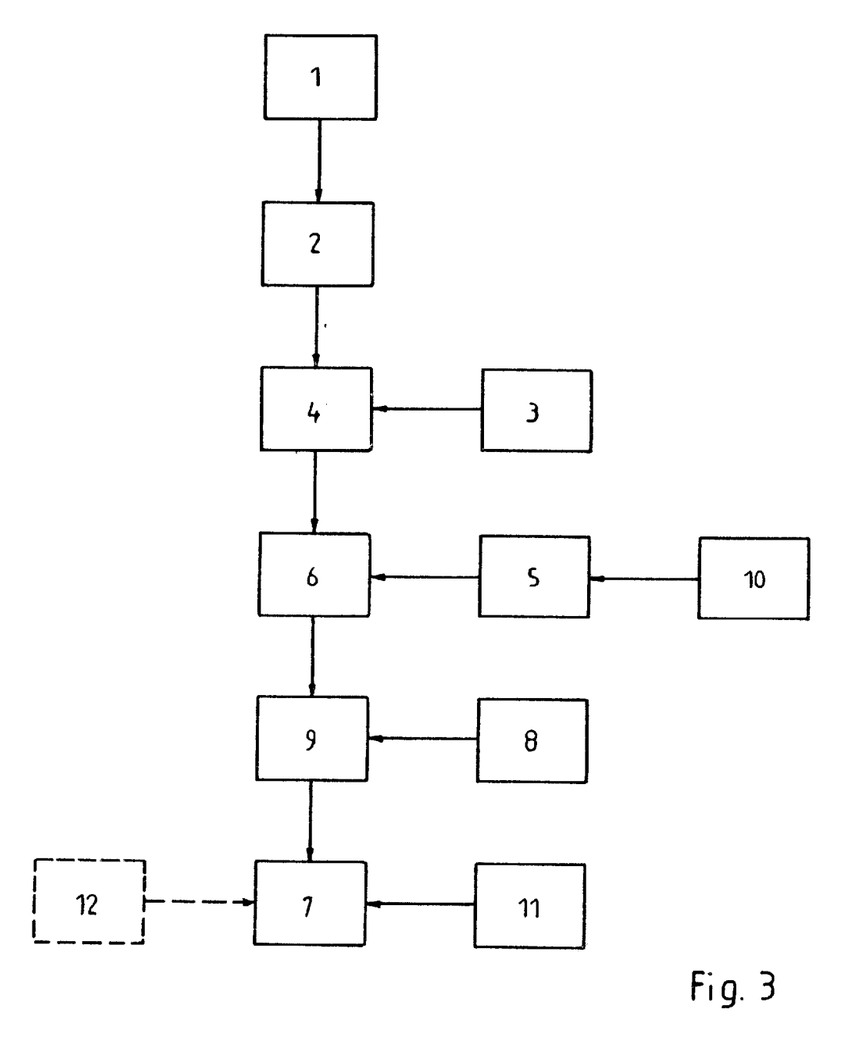
FIG. 3 is a flux diagram of a third embodiment of the new method.

According to FIG. 3, a further step 11 is added to the method according to FIG. 2. In step 10 an integer number N of the hybridization probes to be automatically selected is defined. Correspondingly, in step 7 only a list cf the N top ranked possible hybridization probes is output. Alternatively, in step 7 the possible hybridization probes can be separately ranked for each of the kinds of the oligonucleotide hybridization probes, and the N top ranked possible hybridization probes can be output for each of the kinds of the oligonucleotide hybridization probes.

Further, step 7 can include checking, for each of the possible hybridization probes, whether it is able to hybridize either to the mutant DNA strand and the opposite sense mutant DNA strand, or to the wild-type DNA strand and the opposite sense wild-type DNA strand in more than one way. Then, ranking the possible hybridization probes with regard to the temperature difference may include ranking only those possible hybridization probes which are neither able to hybridize to the mutant DNA strand and the opposite sense mutant DNA strand, nor to the wild-type DNA strand and the opposite sense wild-type DNA strand in more than one way.

In an optional step 12 one or more farther mutations which may occur on the mutant DNA strand or the wild-type DNA-strand or the opposite sense wild-type DNA strand may be defined, so that in step 7 it may be checked, for each of the possible hybridization probes, whether it is sensitive to the further mutation in the same way as to the mutation. Thus ranking the possible hybridization probes with regard to the temperature difference may be limited to ranking only those possible hybridization probes which are not sensitive to the further mutation in the same way as to the mutation.

Further refinements due to special requirements for the possible hybridization probes to be selected are possible and easily accomplished by those skilled in the art Now, a theoretical background is given for the n-n Model to be defined in step 5 of the methods according to FIGS. 1 to 3.

The enthalpy ($\Delta H^\circ$) and entropy ($\Delta S^\circ$) of an oligonucleotide duplex is needed for the calculation of its melting temperature:

$$T_m = \Delta H^\circ / \Delta S^\circ[Na+] + R \times 1n(CT) - 273.15 \quad [Eq\ 1]$$

where R is the gas constant (1.987 cal/K×mol), CT is the strand concentration, $\Delta S^\circ$ [Na] is the entropy at a given sodium equivalent concentration. For non-self-complementary sequences CT is the concentration of oligonucleotides divided by 4. A sequence is considered to be self-complementary if two strands of the same sequence can form a duplex.

For the calculation of Tm $\Delta H^\circ$ needs to be calculated from Eq 2 and $\Delta S^\circ$ [Na] from Eqs 3–5 knowing CT. According to the n-n model, energy for helix formation is the sum of three terms, one for helix propagation energy from the sum of every base pair, one for an energy change caused by helix initiation and one to account for effects caused by duplex formation of self-complementary strands. The following formula applies for the calculation of $\Delta H^\circ$ for an oligonucleotide:

$$\Delta H^\circ_{total} = \Sigma_i n_i \Delta H^\circ(i) + \Delta H^\circ(5'init) + \Delta H^\circ(3'init) + \Delta H^\circ(symmetry) \quad [Eq\ 2]$$

$\Delta H^\circ$ (i) is the enthalpy change for the ten possible n-n and $n_i$ is the number of occurrences of the respective doublet.

For $\Delta S^\circ$ a similar formula applies;

$$\Delta S^\circ_{total} = \Sigma_i n_i \Delta S^\circ(i) + \Delta S^\circ(5'init) + \Delta S^\circ(3'init) + \Delta S^\circ(symmetry) \quad [Eq\ 3]$$

For Eq 2 and Eq 3 it should be noted, that the symmetry correction is zero for non-self-complementary oligonucleotides. IThe $\Delta H^\circ$ and $\Delta S^\circ$ values for Watson-Crick nearest neighbors with matched and mismatched basepairs as well as those for initiation and symmetry correction were taken from published data and are summarized in tables 1 and 2. A standard PCR buffer contains 50 mM KCl and 1.5 mM $Mg^{2+}$, for rapid cycling applications higher Mg concentrations are often used. $Mg^{2+}$ cations have a 140 times higher stabilizing effect on duplexes compared to $Na^+$ [13]. The concentrations of the monovalent ions do not add much to this effect, at least under the conditions which apply for PCR [13]. Therefore the sodium equivalents are calculated as follows:

$$Na^+\ equivalent=[Mg^{2+}] \times 140 \quad [Eq\ 4a]$$

Alternatively a formula based on a 100 times higher DNA stabilizing effect of $Mg^{2+}$ cations may be used. This also takes into account the monovalent ions [14]:

$$Na^+\ equivalent=[Mg^{2+}] \times 100 + monovalent\ ions \quad [Eq\ 4b]$$

The entropy is salt dependent and therefore $\Delta S^\circ$ must be corrected if the sodium concentration is different from 1M NaCl, the condition under which the parameters tabulated in table 1 were derived [5].

$$\Delta S^\circ[Na] = \Delta S^\circ[1M\ Na] + 0.368 \times N \times 1n[Na^+] \quad [Eq\ 5]$$

where N is equal to the oligonucleotide length minus 1.

If DMSO is included in a PCR reaction, it induces a Tm reduction of 0.6° C. for each percent DMSO [15].

1. Example: Calculation of Tm for a 18 mer without Mismatches

As an example the Tm of the 18 mer

Figure 4:
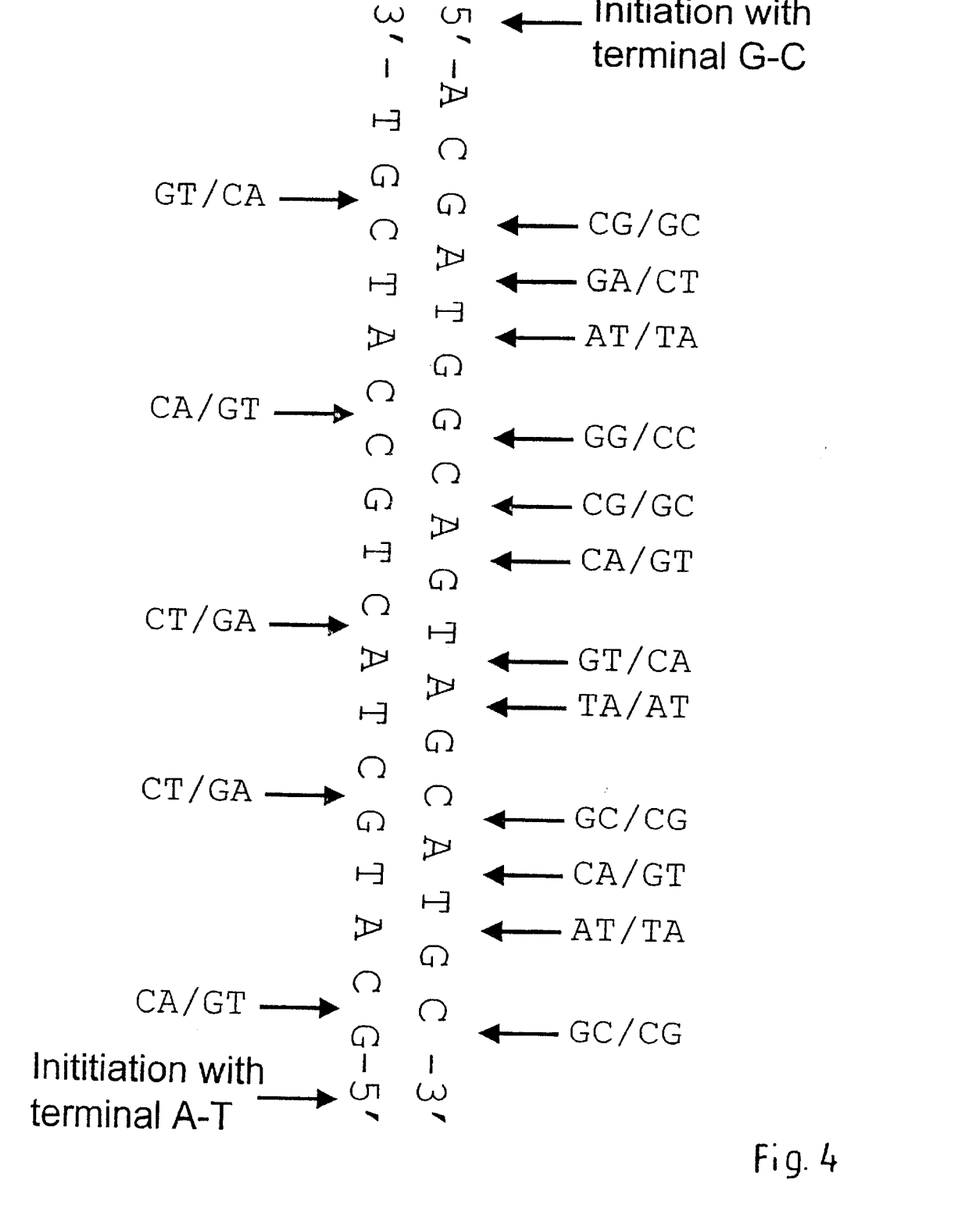
FIG. 4 shows an example DNA duplex of a 18 mer oligonucleotide SEQ ID NO 1, there are 17 n-n doublets and initiation energies for termination with G-C and A-T must be considered; the oligonucleotide is non-self-complementary.

5'-ACG ATG GCA GTA GCA TGC-3' according to FIG. 4 is calculated.

3'-TGC TAC CGT CAT CGT ACG-5'

This example oligonucleotide has 17 n-n doublets. These are AC/TG, CG/GC, GA/CT, AT/TA, TG/AC, GG/CC, GC/CG and so on, see FIG. 4. It should be noted that the first doublet (AC/TG) is identical with GT/CA. Only the thermodynamic data for latter doublet the is listed in table 1 to save space. Palindromic sequences are not listed twice. From the n-n given in table 1, the number of different doublets found in the above 18 mer oligonucleotide are as follows:

$N_{AA/TT}0$, $N_{AT/TA}2$, $N_{TA/AT}1$, $N_{CA/GT}4$, $N_{GT/CA}2$, $N_{CT/GA}2$, $N_{GA/CT}1$, $N_{CG/GC}1$, $N_{GC/CG}3$, $N_{GG/CC}1$.

With data from table 1 $\Delta H^\circ$ can be calculated according to Eq 2:

$\Sigma_i n_i \Delta H^\circ(i)$ results in $0 \times (-7.9) + 2 \times (-7.2) + 1 \times (-7.2) + 4 \times (-8.5) + 2 \times (-8.4) + 2 \times (-7.8) + 1 \times (-8.2) + 1 \times (-10.6) + 3 \times (-9.8) + 1 \times (-8.0) = -144.2$ kcal/mol The initiation term for each direction is 0.1 kcal/mol for initiation with terminal G-C and 2.3 kcal/mol for initiation with terminal A-T.

No symmetry correction is necessary since the oligonucleotide is non-self-complementary.

$$\Delta H^\circ_{total} = -144.2 + 0.1 + 2.3\ kcal/mol = -141.8\ kcal/mol$$

$\Delta S^\circ$ calculation according to Eq 3:

$\Sigma_i n_i \Delta S^\circ(i)$ results in $0 \times (-22.2) + 2 \times (-20.4) + 1 \times (-21.3) + 4 \times (-22.7) + 2 \times (-22.4) + 2 \times (-21.0) + 1 \times (-22.2) + 1 \times (-27.2) + 3 \times (-24.4) + 1 \times (-19.9) = -382.2$ cal/K×mol The initiation term for each direction is −2.8 cal/K×mol for initiation with terminal G-C and 4.1 cal/K×mol for initiation with terminal A-T, total+1.3 cal/K×mol. No symmetry correction is necessary since the oligonucleotide is non-self-complementary.

$$\Delta S^\circ_{total} = -380.9\ cal/K \times mol$$

Sodium equivalents calculation according to Eq 4a:

Assuming the PCR contains 2.5 mM $Mg^{2+}$, according to Eq 4a the sodium equivalent is 2.5 mM×140=350 mM=0.35 M.

Calculating ΔS for a given sodium equivalent according to Eq 5:
For a 18 bp duplex is N=17.

$$\Delta S^0[Na]=-380.9 \text{ cal/K}\times\text{mol}+0.368\times17\times1n[0.35]=-387.5 \text{ cal/K}\times\text{mol}$$

Calculating Tm according to Eq 1
Because of the different units ΔH must be multiplied by 1000 to cal/mol. To convert from Kelvin to Celsius subtract 273.15.

The concentration of the probe is 0.1 μM 0.1×10e-6 M and this must be divided by 4 because the sequence is non-self-complementary.

$$T_m = \frac{-141800 \text{ kal/mol}}{-387.5 \text{ cal/K}\times\text{mol}+1.987 \text{ cal/K}\times\text{mol}\times\ln\left(\frac{0.1\times10^{-6} \text{ mol}}{4}\right)} - 273.15 = 62.7° \text{ C}.$$

2. Example: Calculation of Tm for a 18 mer with Mismatches

As an example the same 18 mer 5'-ACG ATG GCA GTA GCA TGC-3' as above is taken assuming a G→A mutation at the third base. Hybridization of the wild type probe with the mutated strand leads to the following duplex with a G-T mismatch in the trimer CGA/GTT:

5'-ACG ATG GCA GTA GCA TGC-3'
3 -TGT TAC CGT CAT CGT ACG-5'

The oligonucleotide example has 15 Watson-Crick paired doublets (table 1) and 2 mismatched doublets (table 2). These are AC/TG, CG/GT, GA/TT, AT/TA, TG/AC, GG/CC, GC/CG and so on. The number of different doublets are:

$N_{AA/TT}0$, $N_{AT/TA}2$, $N_{TA/AT}1$, $N_{CA/GT}4$, $N_{GT/CA}2$, $N_{CT/GA}1$, $N_{GA/CT}1$, $N_{CG/GC}0$, $N_{GC/CG}3$, $N_{GG/CC}1$. The two doublets affected by the mutation are: $N_{CG/GT}$ and $N_{GA/TT}$. Each of these doublets occurs once. The remaining n-n pairs are equal to example 1.

With data also from table 2 ΔH⁰ can be calculated according to Eq 2:

For the Watson-Crick paired bases $\Sigma_i$ $n_i$ $\Delta H^U$ (i) results in 0×(-7.9)+2×(-7.2)+1×(-7.2)+4×(-8.5)+2×(-8.4)+2×(-7.8)+0×(-8.2)+0×(-10.6)+3×(-9.8)+1×(-8.0)=-125.4 kcal/mol. Two doublets are affected by mismatches and their thermodynamic properties are found in table 2. For the CG/GT doublet ΔH⁰=-4.1 kcal/mol, for GA/TT (look up TT/GA in table 2, this is the same as GA/TT) ΔH⁰=-1.3 kcal/mol.

Furthermore, the initiation term is added for each direction, that is 0.1 kcal/mol for initiation with terminal G-C and 2.3 kcal/mol for initiation with terminal A-T.

No symmetry correction is necessary as the oligonucleotide is non-self-complementary.

$$\Delta H^0_{total}=-125.4-4.1-1.3+0.1+2.3=-128.4 \text{ kcal/mol}$$

ΔS⁰ calculation according to Eq 3:
For the Watson-Crick paired bases $\Sigma_i$ $n_i$ $\Delta S^0(i)$ results in 0×(-22.2)+2×(-20.4)+1×(-21.3)+4×(-22.7)+2×(-22.4)+2×(-21.0)+0×(-22.2)+0×(-27.2)+3×(-24.4)+1×(-19.9)=-332.8 cal/K×mol. Two doublets are affected by mismatches and their thermodynamic properties are again found in table 2. For the CG/GT doublet ΔS⁰=-11.7 kcal/K×mol, for GA/TT (look up TT/GA in table 2, this is the same as GA/TT) ΔS⁰=-5.3 kcal/K×mol.

The initiation term is added for each direction, that is -2.8 cal/K×mol for initiation with terminal G-C and 4.1 cal/K×mol for initiation with terminal A-T.

No symmetry correction is necessary as the oligonucleotide is non-self-complementary.

$$\Delta S^0_{total}=-348.5 \text{ cal/K}\times\text{mol}$$

Sodium equivalents calculation according to Eq 4a:
Conditions are the same as above: 2.5 mM $Mg^{2+}$, according to Eq 4a the sodium equivalent is 2.5 mM×140=350 mM=0.35 M.

Calculating ΔS⁰ for a given sodium equivalent according to Eq 5:
For a 18 bp duplex is N=17.

$$\Delta S^0[Na]=-348.5 \text{ cal/K}\times\text{mol}+0.368\times17\times1n[0.35]=-355.1 \text{ cal/K}\times\text{mol}$$

Calculating Tm according to Eq 1
Again ΔH⁰ must be multiplied with 1000 to change to cal/mol. 273.15 is subtracted to convert from Kelvin to Celsius. The concentration of the probe is 0.1 μM=0.1×10e-6 M and this must be divided by 4 because the sequence is non-self-complementary.

$$T_m = \frac{-128400 \text{ kal/mol}}{-355.1 \text{ cal/K}\times\text{mol}+1.987 \text{ cal/K}\times\text{mol}\times\ln\left(\frac{0.1\times10^{-6} \text{ mol}}{4}\right)} - 273.15 = 56.2° \text{ C}.$$

3. Example: Calculation of ΔTm for a Hybridization Probe Mutation Detection Assay In the first example a Tm of 62.7° C. was calculated for a 18 mer probe. In the second calculation a lower Tm of 56.2° C. was calculated due to a single mismatch caused by a G→A mutation. If the former probe were to hybridize on the latter mutated strand, a calculated reduction in Tm of 6.5° C. would result.

The thermodynamic calculations assume that the annealing occurs at pH 7.0. This is not the case in standard PCR buffer systems, but the resulting error seems to be small. More important is to note that mismatches in the terminal and penultimate position are not properly reflected by the parameters in table 2 [3;10]. The thermodynamic data set for double mismatches (i.e., immediately adjacent mismatches) is still incomplete. Only for the few double mismatches listed in table 2 is a reliable prediction possible. The influence of the salt concentration on oligonucleotide stability is also still under investigation [4;5;13]. Nevertheless, the methods presented here will allow a reliable estimate of hybridization probe Tm on the LightCycler but may require correction of the sodium equivalents according to the local PCR conditions.

4. Validation of the n-n Model on the LightCycler

Figure 5:
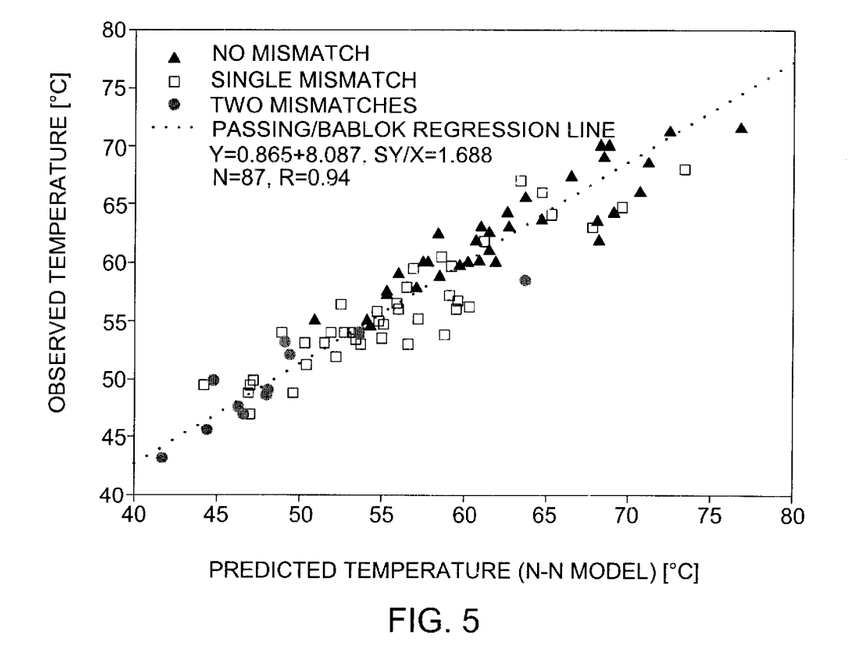
FIG. 5 is a diagram of experimentally observed melting points versus melting points calculated with the n-n model; the regression was calculated according to Passing and Bablok [33], while the standard error of the estimate (SY1) was calculated with the principal component method.
Figure 6:
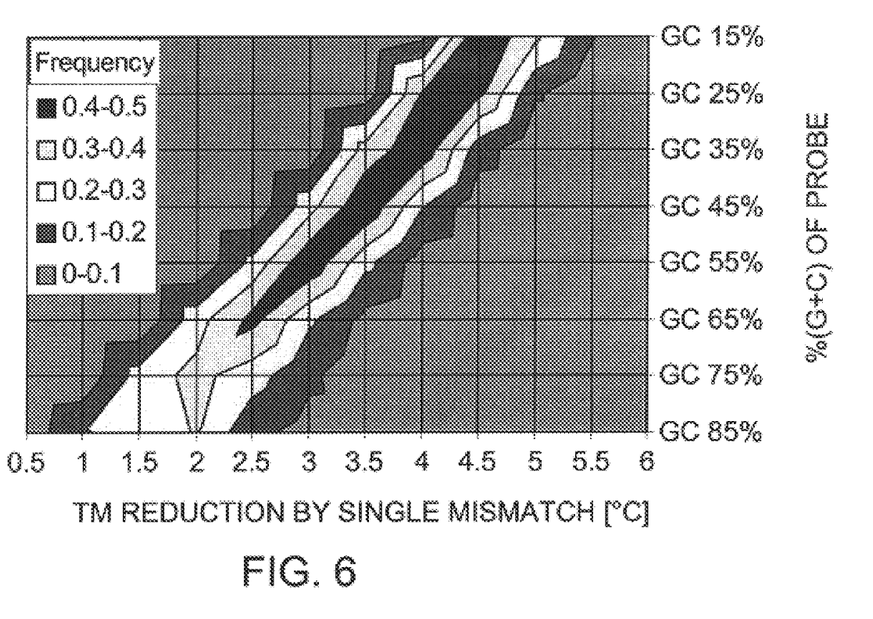
FIG. 6 is a contour plot showing the interdependence of the melting temperature shift of 19 mer probes destabilized by 3 single mutation versus their GC content the different frequencies are shown in shadings.

The formulas described above were incorporated into a Microsoft®Excel® spreadsheet software which is capable of calculating the thermodynamic data for matched and mismatched oligonucleotides under different concentrations and ionic strengths. This program is available for download via http://server1.medikc.med.uni-goettingen.de/meltcalc.htm or it may be requested by email. A total of 87 melting points resulting from eleven different published [16–26] and 14 unpublished hybridization probe assays where calculated and showed an excellent fit with the predictions from the n-n model, as may be seen from FIG. 5. For the data shown in FIG. 5 Eq. 4b was used to calculate the $Na^+$ equivalents which gave a better fit when using the published Tm data from different laboratories. However, under the standard PCR conditions used with 2.5 mM $Mg^{2+}$ and 5% DMSO the best prediction were obtained using Eq 4a.

Genotyping assays for the apolipoprotein B-3500 and factor V Leiden mutation have been performed. For both loci different mutations have been described that occur under the detection probe. These are the G10699A and C10698T mutations of apolipoprotein B [27] and the G1691A, A1692C and G1689A mutations for factor V [20;28]. Increasing knowledge on the prevalence of single nucleotide polymorphisms in the human genome [29;30] raises the important question about the sensitivity of hybridization probe assays towards different mutations under a probe. Melting point calculations for different possible mutations under a 19 mer probe led us speculate that no mutation under a properly designed probe will remained undetected. However, there are different mutations possible that destabilize the probe binding to the same extent [12]. These mutations will not be discriminated from each other. FIG. 3 shows how 19 mer probes with different GC content are destabilized by a single base mutation. The most important trend is that probes with higher GC content show less Tm shift due to a single mutation. Another principal point is that shorter probes show higher Tm shifts because the destabilizing impact of the mutation on the total stability is higher in shorter duplexes. The thermodynamic n-n model provides the theoretical basis for the stability of matched and mismatched oligonucleotides. The comparison of experimentally derived melting points with those calculated from the n-n model show very good agreement. Using a detection probe that has been properly optimized according to this model it may be appriciated that the detection of every point mutation should be possible. However, it is possible that different mutations under a probe result in the same Tm reduction. Important factors for the design of hybridization probes are: (I.) Absence of significant self- or cross dimerization of probes and amplification primers. (II.) Equal melting points of detection and anchor probe and absence of false priming sites on the amplicon for hybridization probes used for quantification. (III.) Use of a detection probe with a maximum Tm shift caused by the investigated mutation (see below) and an anchor probe with a Tm approximately 10% higher than that of the detection probe for mutation detection. Provided it is not in the penultimate or ultimate position the place where the mutation is located under the probe is not important. The resulting melting point shift will be affected by the type of mutation and the neighboring bases but not significantly by the position itself. The commonest mutations are G→A mutations [31]. However, the resulting G:T mismatch under the probe is among the most stable mismatches which occur together with G:A and G:G mismatches [9]. It is therefore advisable to place the detection probe on the antisense strand. The resulting complementary C:A mismatch has a higher destabilizing effect and is more readily detected. (IV.) The gap between the fluorophores should be as small as possible since the FRET efficiency is inversely proportional to the sixth power of the distance between the donor and the acceptor dye [32]. One to five basepairs gap has been reported to give good results [1].

REFERENCES

1. Caplin B E, Rasmussen A, Bernard P S, Wittwer C T (1999) LightCycler hybridization probes. *Biochemica* 1: 5–8
2. Gray D M (1997) Derivation of nearest-neighbor properties from data on nucleic acid oligomers. I. Simple sets of independent sequences and the influence of absent nearest neighbors. *Biopolymers* 42: 783–793
3. Allawi H T, SantaLucia J, Jr. (1997) Thermodynamics and NMR of internal G.T mismatches in DNA. Biochemistry 36: 10581–10594
4. SantaLucia J, Jr., Allawi H T, Seneviratne P A (1996) Improved nearest-neighbor parameters for predicting DNA duplex stability. Biochemistry 35: 3555–3562
5. SantaLucia J, Jr. (1998) A unified view of polymer, dumbbell, and oligonucleotide DNA nearest-neighbor thermodynamics. Proc Natl Acad Sci USA 95: 1460–1465
6. Sugimoto N, Nakano S, Yoneyama M, Honda K (1996) Improved thermodynamic parameters and helix initiation factor to predict stability of DNA duplexes. Nucleic Acids Res 24: 4501–4505
7. Allawi H T, SantaLucia J, Jr. (1998) Nearest-neighbor thermodynamics of internal A.C mismatches in DNA: sequence dependence and pH effects. Biochemistry 37: 9435–9444
8. Allawi H T, SantaLucia J, Jr. (1998) Thermodynamics of internal C.T mismatches in DNA. Nucleic Acids Res 26: 2694–2701
9. Allawi H T, SantaLucia J, Jr. (1998) Nearest neighbor thermodynamic parameters for internal G.A mismatches in DNA. Biochemistry 37: 2170–2179
10. Peyret N, Seneviratne P A, Allawi H T, SantaLucia J, Jr. (1999) Nearest-neighbor thermodynamics and NMR of DNA sequences with internal A.A, C.C, G.G, and T.T mismatches. Biochemistry 38: 3468–3477
11. Owczarzy R, Valloe P M, Gallo F J, Paner T M, Lane M J, Benight A S (1997) Predicting sequence-dependent melting stability of short duplex DNA oligomers. Biopolymers 44: 217–239
13. Nakano S, Fujimoto M, Hara H, Sugimoto N (1999) Nucleic acid duplex stability: influence of base composition on cation effects. Nucleic Acids Res 27: 2957–2965
14. Chester N, Marshak D R (1993) Dimethyl sulfoxide-mediated primer Tm reduction: a method for analyzing the role of renaturation temperature in the polymerase chain reaction. Anal Biochem 209: 284–290
15. Musielski H, Mann W, Laue R, Michel S (1981) Influence of dimethylsulfoxide on transcription by bacteriophage T3-induced RNA polymerase. Z Alig Mikrobiol 21: 447–456
16. Bernard P S, Lay M J, Wittwer C T (1998) Integrated amplification and detection of the C677T point mutation in the methylenetetrahydrofolate reductase gene by fluorescence resonance energy transfer and probe melting curves. Anal Biochem 255: 101–107
17. Bernard P S, Ajioka R S, Kushner J P, Wittwer C T (1998) Homogeneous multiplex genotyping of hemochromatosis mutations with fluorescent hybridization probes. Am J Pathol 153: 1055–1061
18. Bernard P S, Pritham G H, Wittwer C T (1999) Color Multiplexing Hybridization Probes Using the Apolipoprotein E Locus as a Model System for Genotyping. Anal Biochem 273: 221–228
19. Lay M J, Wittwer C T (1997) Real-time fluorescence genotyping of factor V Leiden during rapid-cycle PCR. Clin Chem 43: 2262–2267
20. Lyon E, Millson A, Phan T, Wittwer C T (1998) Detection and Identification of Base Alterations Within the Region of Factor V Leiden by Fluorescent Melting Curves. Mol Diagn 3: 203–209

21. Aslanidis C, Schmitz G (1999) High-speed apolipoprotein E genotyping and apolipoprotein B3500 mutation detection using real-time fluorescence PCR and melting curves. Clin Chem 45: 1094–1097
22. Aslanidis C, Nauck M, Schmitz G (1999) High-speed prothrombin G→A 20210 and methylenetetrahydrofolate reductase C→T 677 mutation detection using real-time fluorescence PCR and melting curves. Biotechniques 27: 234–6, 238
23. Gaffney D, Reid J M, Cameron I M, Vass K, Caslake M J, Shepherd J, Packard C J (1995) Independent mutations at codon 3500 of the apolipoprotein B gene are associated with hyperlipidemia. Arterioscler Thromb Vasc Biol 15: 1025–1029
24. von Ahsen N, Schütz E, Armstrong V W, Oellerich M (1999) Rapid detection of prothrombotic mutations of prothrombin (G20210A), factor V (G1691A) and methylenetetrahydrofolate reductase (C677T) by real time fluorescence PCR with the LightCycler. Clin Chem 45: 694–696
25. Nauck M, Wieland H, März W (1999) Rapid, Homogeneous Genotyping of the 4G/5G Polymorphism in the Promoter Region of the PAI1 Gene by Fluorescence Resonance Energy Transfer and Probe Melting Curves. Clin Chem 45, 1141–1147
26. Nauck M S, Gierens H, Nauck M A, Marz W, Wieland H (1999) Rapid genotyping of human platelet antigen 1 (HPA-1) with fluorophore-labelled hybridization probes on the LightCycler. Br J Haematol 105: 803–810
27. Tybjaerg-Hansen A, Steffensen R, Meinertz H, Schnohr P, Nordestgaard B G (1998) Association of mutations in the apolipoprotein B gene with hypercholesterolemia and the risk of ischemic heart disease. N Engl J Med 338: 1577–1584
28. Liebman H A, Sutherland D, Bacon R, McGehee W (1996) Evaluation of a tissue factor dependent factor V assay to detect factor V Leiden: demonstration of high sensitivity and specificity for a generally applicable assay for activated protein C resistance. Br J Haematol 95: 550–553
29. Cargill M, Altshuler D, Ireland J, Sklar P, Ardlie K, Patil N, Lane C R, Lim E P, Kalayanaraman N, Nemesh J, Ziaugra L, Friedland L, Rolfe A, Warrington J, Lipshutz R, Daley G Q, Lander E S (1999) Characterization of single-nucleotide polymorphisms in coding regions of human genes. Nat Genet 22: 231–238
30. Brown S M (1 999) Snapping up SNPs. Biotechniques 26: 1090–1093
31. Cooper, D. N., Krawczal, M., and Antonarakis, S. E. (1995): The nature and mechanism of human gene mutation. In: The metabolic and molecular bases of inherited disease, edited by C. R. Scriver, et al, pp. 259–291, McGraw-Hill, New York.
32. Clegg R M (1995) Fluorescence resonance energy transfer. Curr Opin Biotechnol 6: 103–110
33. Passing H, Bablok W (1984) Comparison of several regression procedures for method comparison studies and determination of sample sizes. Application of linear regression procedures for method comparison studies in Clinical Chemistry, Part II. J Clin Chem Clin Biochem 22; 431–445

TABLE 1

Unified parameters for oligonucleotide $\Delta H^\circ$ and $\Delta S^\circ$ in 1M NaCl [5].
(Nearest neighbor dimer duplexes are presented with a slash separating strands in antiparallel orientation, e.g. AT/TA means 5'-AT-3' Watson-Crick paired with 3'-TA-5'.)

| Sequence | $\Delta H^\circ$ kcal/mol | $\Delta S^\circ$ cal/Kxmol |
| --- | --- | --- |
| AA/TT | −7.9 | −22.2 |
| AT/TA | −7.2 | −20.4 |
| TA/AT | −7.2 | −21.3 |
| CA/GT | −8.5 | −22.7 |
| GT/CA | −8.4 | −22.4 |
| CT/GA | −7.8 | −21.0 |
| GA/CT | −8.2 | −22.2 |
| CG/GC | −10.6 | −27.2 |
| GC/CG | −9.8 | −24.4 |
| GG/CC | −8.0 | −19.9 |
| Initiation with terminal G-C | 0.1 | −2.8 |
| Initiation with terminal A-T | 2.3 | 4.1 |
| Symmetry correction for self complimentary oligos | 0 | −1.4 |

TABLE 2

Parameters for mismatched oligonucleotide $\Delta H^\circ$ and $\Delta S^\circ$ in 1M NaCl.
(References are given in the table. Nearest neighbor dimer duplexes are presented with a slash separating strands in antiparallel orientation e.g. AT/TG means 5'-AT-3' mismatched with 3'-TG-5'. Mismatches are in the second position of the listed doublet except for double mismatches. These parameters are not valid for the calculation of mismatches in the terminal or penultimate position.)

| Sequence | $\Delta H^\circ$ kcal/mol | $\Delta S^\circ$ cal/Kxmol |
| --- | --- | --- |
| Internal G-A mismatches [9] | | |
| AA/TG | −0.6 | −2.3 |
| AG/TA | −0.7 | −2.3 |
| CA/GG | −0.7 | −2.3 |
| CG/GA | −4.0 | −13.2 |
| GA/CG | −0.6 | −1.0 |
| GG/CA | 0.5 | 3.2 |
| TA/AG | 0.7 | 0.7 |
| TG/AA | 3.0 | 7.4 |
| Internal C-T mismatches [8] | | |
| AC/TT | 0.7 | 0.2 |
| AT/TC | −1.2 | −6.2 |
| CC/GT | −0.8 | −4.5 |
| CT/GC | −1.5 | −6.1 |
| GC/CT | 2.3 | 5.4 |
| GT/CC | 5.2 | 13.5 |
| TC/AT | 1.2 | 0.7 |
| TT/AC | 1.0 | 0.7 |
| Internal A-C mismatches [7] | | |
| AA/TC | 2.3 | 4.6 |
| AC/TA | 5.3 | 14.6 |
| CA/GC | 1.9 | 3.7 |
| CC/GA | 0.6 | −0.6 |
| GA/CC | 5.2 | 14.2 |
| GC/CA | −0.7 | −3.8 |
| TA/AC | 3.4 | 8.0 |
| TC/AA | 7.6 | 20.2 |

TABLE 2-continued

Parameters for mismatched oligonucleotide $\Delta H^o$ and $\Delta S^o$ in 1M NaCl.
(References are given in the table. Nearest neighbor dimer duplexes are presented with a slash separating strands in antiparallel orientation e.g. AT/TG means 5'-AT-3' mismatched with 3'-TG-5'. Mismatches are in the second position of the listed doublet except for double mismatches. These parameters are not valid for the calculation of mismatches in the terminal or penultimate position.)

| Sequence | $\Delta H^o$ kcal/mol | $\Delta S^o$ cal/Kxmol |
|---|---|---|
| Internal G-T mismatches [3] | | |
| AG/TT | 1.0 | 0.9 |
| AT/TG | −2.5 | −8.3 |
| GG/GT | −4.1 | −11.7 |
| CT/GG | −2.8 | −8.0 |
| GG/CT | 3.3 | 10.4 |
| GT/CG | −4.4 | −12.3 |
| TG/AT | −0.1 | −1.7 |
| TT/AG | −1.3 | −5.3 |
| Internal A-A mismatches [10] | | |
| AA/TA | 1.2 | 1.7 |
| CA/GA | −0.9 | −4.2 |
| GA/CA | −2.9 | −9.8 |
| TA/AA | 4.7 | 12.9 |
| Internal C-C mismatches [10] | | |
| AC/TC | 0.0 | −4.4 |
| CC/GC | −1.5 | −7.2 |
| GC/CC | 3.6 | 8.9 |
| TC/AC | 6.1 | 16.4 |
| Internal G-G mismatches [10] | | |
| AG/TG | −3.1 | −9.5 |
| CG/GG | −4.9 | −15.3 |
| GG/CG | −6.0 | −15.8 |
| TG/AG | 1.6 | 3.6 |
| Internal T-T mismatches [10] | | |
| AT/TT | −2.7 | −10.8 |
| CT/GT | −5.0 | −15.8 |
| GT/CT | −2.2 | −8.4 |
| TT/AT | 0.2 | −1.5 |
| Double mismatches [3] | | |
| GG/TT | 5.8 | 16.3 |
| GT/TG | 4.1 | 9.5 |
| TG/GT | −1.4 | −6.2 |

What is claimed is:

1. A method of selecting oligonucleotide hybridization probes for detecting a mutation causing a mismatch in a DNA duplex, the method comprising the steps of:
defining the mutation to be detected by
a DNA sequence of a mutant DNA strand and
a DNA sequence of a wild-type DNA strand corresponding to the mutant DNA strand;
defining an integer variable L1 for a first length of the oligonucleotide hybridization probes from the place of mutation in a first direction;
defining a range from m1 to n1 of possible values of the variable L1;
defining an integer variable L2 for a second length of the oligonucleotide hybridization probes from the place of mutation in a second direction opposite to the first direction;
defining a range from m2 to n2 of possible values of the variable L2;
selecting at least one oligonucleotide hybridization probe from the group consisting of
probes which are fully complementary to the mutant DNA strand,
probes which are fully complementary to the wild-type DNA strand corresponding to the mutant DNA strand,
probes which are fully complementary to an opposite sense mutant DNA strand which is the complementary DNA strand to the mutant DNA strand, and
probes which are fully complementary to an opposite sense wild-type DNA strand which is the complementary DNA strand to the wild-type DNA strand corresponding to the mutant DNA strand;
determining all possible hybridization probes from the possible values of the variables L1 and L2, and the selected probes;
defining a thermodynamic nearest-neighbor model for calculating a melting point of a certain hybridization probe hybridized to a DNA strand, the melting point being a temperature at which a predetermined percentage of a multitude of identical pairs of said certain hybridization probe and said DNA strand is in an annealed state;
calculating, on basis of the thermodynamic nearest-neighbor model, for all possible hybridization probes
a first melting point of the respective probe hybridized with its complementary mutant DNA strand or opposite sense mutant DNA strand, respectively,

SEQUENCE LISTING

<160> NUMBER OF SEQ ID NOS: 1

<210> SEQ ID NO 1
<211> LENGTH: 18
<212> TYPE: DNA
<213> ORGANISM: Homo sapiens

<400> SEQUENCE: 1
gcatgctact gccatcgt                                             18 a second melting point of the respective probe hybridized with its complementary wild-type DNA strand or opposite sense wild-type DNA strand, respectively, and a temperature difference between the second melting point and the first melting point; and ranking the possible hybridization probes with regard to the temperature difference.

2. The method of claim 1, and further comprising the steps of:

defining a temperature range of a hybridization assay to be employed for detecting the mutation using the oligonucleotide hybridization probes; and checking for each of the possible hybridization probes whether both the first and the second melting points are within the temperature range of the hybridization assay;

wherein the step of ranking the possible hybridization probes with regard to the temperature difference includes:

ranking only those possible hybridization probes which have both their melting points within the temperature range of the hybridization assay.

3. The method of claim 2, wherein the step of defining the temperature range of the hybridization assay to be employed for detecting the mutation includes:

defining the temperature range within a range from 20 to 80° C.

4. The method according to claim 1, and further comprising the step of:

defining at least one physico-chemical parameter of a hybridization assay to be employed for detecting the mutation using the oligonucleotide hybridization probes;

wherein the step of defining a thermodynamic nearest-neighbor model includes:

defining the thermodynamic nearest-neighbor model based on at least one physico-chemical parameter of the hybridization assay.

5. The method of claim 4, wherein the step of defining at least one physico-chemical parameter of the hybridization assay to be employed for detecting the mutation includes:

defining at least one ion concentration as one of the physico-chemical parameters.

6. The method of claim 5, wherein the step of defining at least one ion concentration as one of the physico-chemical parameters includes:

defining a Na+ cation equivalent concentration.

7. The method according to claim 1, and further comprising the steps of:

defining an integer number N of the hybridization probes to be automatically selected; and making a list of the N top ranked possible hybridization probes.

8. The method according to claim 1, wherein the step of ranking the possible hybridization probes with regard to the temperature difference includes:

ranking the possible hybridization probes separately for each of the kinds of the oligonucleotide hybridization probes.

9. The method according to claim 1, and further comprising the step of:

checking, for each of the possible hybridization probes, whether it is able to hybridize either to the mutant DNA strand and the opposite sense mutant DNA strand, or to the wild-type DNA strand and the opposite sense wild-type DNA strand in more than one way;

wherein the step of ranking the possible hybridization probes with regard to the temperature difference includes:

ranking only those possible hybridization probes which are neither able to hybridize to the mutant DNA strand and the opposite sense mutant DNA strand, nor to the wild-type DNA strand and the opposite sense wild-type DNA strand in more than one way.

10. The method according to claim 1, and further comprising the steps of:

defining at least one further mutation which may occur on the mutant DNA strand or the wild-type DNA-strand or the opposite sense wild-type DNA strand;

checking, for each of the possible hybridization probes, whether it is sensitive to the further mutation in the same way as to the mutation;

wherein the step of ranking the possible hybridization probes with regard to the temperature difference includes:

ranking only those possible hybridization probes which are not sensitive to the further mutation in the same way as to the mutation.

* * * * *